United States Patent
Herold et al.

(10) Patent No.: US 6,777,574 B1
(45) Date of Patent: Aug. 17, 2004

(54) 2-ALKYL-5-HALOGEN-PENT-4-ENE CARBOXYLIC ACIDS AND THEIR PRODUCTION

(75) Inventors: Peter Herold, Basel (CH); Stefan Stutz, Basel (CH)

(73) Assignee: Speedel Pharma AG, Basel (CH)

( * ) Notice: Subject to any disclaimer, the term of this patent is extended or adjusted under 35 U.S.C. 154(b) by 91 days.

(21) Appl. No.: 10/048,290

(22) PCT Filed: Jul. 13, 2000

(86) PCT No.: PCT/CH00/00385

§ 371 (c)(1),
(2), (4) Date: Jan. 29, 2002

(87) PCT Pub. No.: WO01/09079

PCT Pub. Date: Feb. 8, 2001

(30) Foreign Application Priority Data

Jul. 29, 1999 (CH) .............................. 1401/99
Jan. 11, 2000 (CH) ................................ 44/00

(51) Int. Cl.$^7$ ............................................. C07C 69/00
(52) U.S. Cl. ....................... 560/129; 560/205; 560/219; 562/400; 562/507; 562/510
(58) Field of Search ................. 560/129, 205, 560/219; 562/400, 507, 510, 506; 360/219

(56) References Cited

U.S. PATENT DOCUMENTS 4,291,057 A * 9/1981 Wheeler ..................... 514/521
4,492,799 A * 1/1985 Wheeler ..................... 562/506

OTHER PUBLICATIONS

Chemical Abstracts, vol. 55, No. 21 (1961).
Chemical Abstracts, vol. 70, No. 23 (1969).

* cited by examiner

*Primary Examiner*—Rita Desai
*Assistant Examiner*—Hector M. Reyes
(74) *Attorney, Agent, or Firm*—Wenderoth, Lind & Ponack, L.L.P.

(57) ABSTRACT

Compounds of formula I in the form of their racemates or enantiomers,

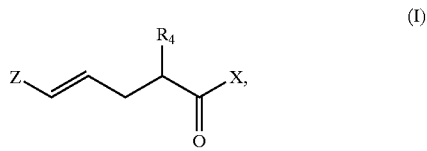
(I)

preferably compounds of formula Ia

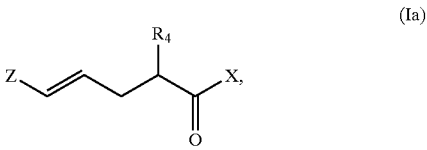
(Ia)

wherein $R_4$ is $C_1$–$C_6$alkyl, Z is chlorine, bromine or iodine, and X is —OH, chloride, bromide or iodide, or X forms an ester group with the carbonyl substituent, as well as salts of carboxylic acids. The compounds are valuable intermediates for the propagation of δ-amino-γ-hydroxy-ω-aryl-alkanecarboxamides, which exhibit renin-inhibiting properties and could be used as antihypertensive agents in pharmaceutical preparations.

14 Claims, No Drawings

2-ALKYL-5-HALOGEN-PENT-4-ENE CARBOXYLIC ACIDS AND THEIR PRODUCTION

This application is a 371 application of PCT/CH00/00385 filed Jul. 13, 2000.

The invention relates to 2-alkyl-5-halogen-pent-4-enecarboxylic acid and its esters and salts in the form of its racemates and enantiomers and a process for the preparation of these carboxylic acids.

In the EP-A-0 678 503, δ-amino-γ-hydroxy-ω-aryl-alkanecarboxamides are described, which exhibit renin-inhibiting properties and could be used as antihypertensive agents in pharmaceutical preparations. The manufacturing procedures described are unsatisfactory in terms of the number of process steps and yields and are not suitable for an industrial process. A disadvantage of these processes is also that the total yields of pure diastereomers that are obtainable are too small.

In a new process, one starts from 2,7-dialkyl-8-aryl-4-octenoyl amides, whose double bond is simultaneously halogenated in the 5-position and hydroxylated in the 4-position under lactonization, then the halogen is substituted by azide, the lactone amidated and the azide then transferred to the amine group. The desired alkanecarboxamides are obtained with the new process both in high total yields and in a high degree of purity, and selectively pure diastereomers can be prepared. The halolactonization of process step a), the azidation of process step b), and the azide reduction of process stop d) are described by P. Herold in the Journal of Organic Chemistry, Vol. 54 (1989), pages 1178–1185.

The 2,7-dialkyl-8-aryl-4-octenoyl amides may correspond for example to formula A,

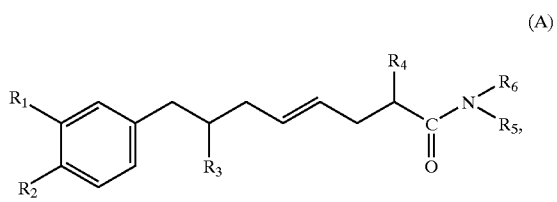

(A)

and especially to formula A1

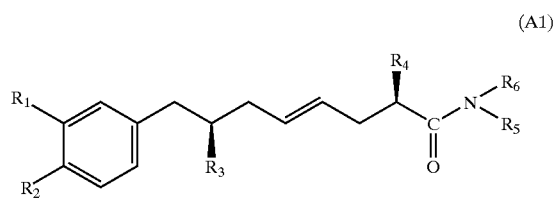

(A1)

wherein $R_1$ and $R_2$ independently of one another are H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_6$ is $C_1$–$C_6$alkyl, $R_5$ is $C_1$–$C_6$alkyl or $C_1$–$C_6$alkoxy, or $R_5$ and $R_6$ together are tetramethylene, pentamethylene, 3-oxa-1,5-pentylene or —$CH_2CH_2O$—C(O)— substituted if necessary with $C_1$–$C_4$alkyl, phenyl or benzyl.

The compounds of formulae A and A1 are obtainable by reacting a compound of formula B

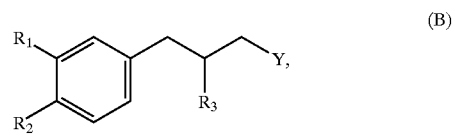

(B)

as racemate or enantiomer, with a compound of formula C, as racemate or enantiomer,

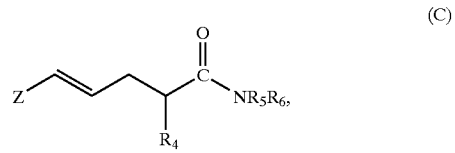

(C)

wherein $R_1$ to $R_4$, $R_5$ and $R_6$ are as defined above, Y is Cl, Br or I and Z is Cl, Br or I, in the presence of an alkali metal or alkaline earth metal. Y and Z are preferably Br and especially Cl.

It is expedient to prepare the compounds of formula C from the carboxylic acids corresponding to the amides, and their esters or acid halides, and these thus represent valuable intermediates for the preparation of the antihypertensive compositions mentioned previously. The formation of carboxamides from carboxylic acid esters and amines in the presence of trialkyl aluminium or dialkyl aluminium halide, for example using trimethyl aluminium or dimethyl aluminium chloride, is described by S. M. Weinreb in Org. Synthesis, VI, page 49 (1988).

A further object of the invention is represented by compounds of formula I in the form of racemates and enantiomers,

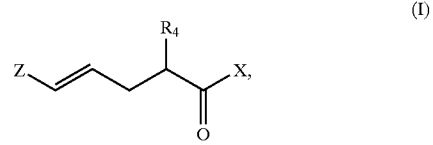

(I)

wherein $R_4$ is $C_1$–$C_6$alkyl, Z is chlorine, bromine or iodine, and X is —OH, chloride, bromide or iodide, or X forms an ester group with the carbonyl substituent as well as salts of carboxylic acids.

Especially preferred enantiomers are those of formula Ia

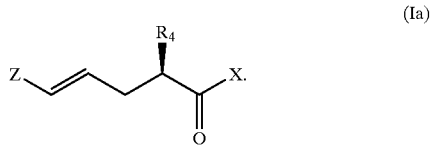

(Ia)

$R_4$ is preferably $C_1$–$C_4$alkyl. Examples of alkyl are methyl, ethyl, n- and i-propyl, n-, i- and t-butyl, pentyl and hexyl. It is very particularly preferred when $R_4$ is i-propyl.

It is especially preferred when Z is Cl.

In the ester group, X is preferably a substituent of formula $R_7O$—, where $R_7$ is an organic group with 1 to 18, preferably 1 to 12, and especially preferably 1 to 8 C-atoms and it necessary comprises heteroatoms selected from group O and N.

$R_7$ may be a branched and preferably linear alkyl, preferably comprising 1 to 4 C-atoms. Examples are methyl, ethyl, n-propyl, n-butyl, pentyl, hexyl, heptyl and octyl. Especially preferred are methyl and ethyl. The alkyl may be substituted, for example with $C_1$–$C_4$alkoxy, such as methoxy or ethoxy. Examples of substituted alkyl are methoxethyl and ethoxyethyl.

$R_7$ may be cycloalkyl with 3 to 8, and preferably 5 or 6 ring-carbon atoms. Examples are cyclopropyl, cyclobutyl, cyclohexyl, cyclopentyl, cyclohexyl, cycloheptyl and cyclooctyl. The cycloalkyl may be substituted with $C_1$–$C_4$alkyl or $C_1$–$C_4$alkoxy.

$R_7$ may be cycloalkyl-$C_1$–$C_4$alkyl with 3 to 8, and preferably 5 or 6 ring-carbon atoms, which is unsubstituted or substituted with $C_1$–$C_4$alkyl or $C_1$–$C_4$alkoxy. Examples are cyclopentylmethyl, cyclohexylmethyl, methylcyclohexylmethyl and cyclohexylethyl.

$R_7$ may be $C6$–$C_{10}$aryl which is unsubstituted or substituted with $C_1$–$C_4$alkyl or $C_1$–$C_4$alkoxy. Examples are phenyl, naphthyl, methylphenyl, ethylphenyl and i-propylphenyl.

$R_7$ may be $C_6$–$C_{10}$aryl-$C_1$–$C_4$alkyl which is unsubstituted or substituted with $C_1$–$C_4$alkyl or $C_1$–$C_4$alkoxy. Examples are benzyl, methylbenzyl and phenylethyl.

Of the acid halides of formula I, the chlorides and bromides are preferred.

The salts of carboxylic acids may for example be alkali metal or alkaline earth metal salts, as well as ammonium salt. Of the alkali metals and alkaline earth metals, lithium, sodium, potassium, magnesium and calcium are preferred. Suitable forms of ammonium are the ammonium cation, the cations of primary, secondary, and tertiary amines, and quaternary ammonium; these cations may comprise 1 to 20, preferably 1 to 16 C-atoms.

Especially preferred compounds of formulae I and Ia are those wherein Z is chlorine, $R_4$ is $C_1$–$C_4$alkyl and especially preferably i-propyl, and X is OH, Cl, Br or $C_1$–$C_4$alkoxy.

A particularly preferred embodiment includes compounds of formulae I and Ia wherein Z is chlorine, $R_4$ is i-propyl, and X is OH, Cl, Br, methoxy or ethoxy.

Especially preferred are compounds of formulae I and Ia wherein Z is chlorine, $R_4$ is i-propyl, and X is Cl or ethoxy.

The compounds of formula I are obtainable for example by reacting isovaleric acid esters with 1,3-dihalogenpropene in the presence of strong amine bases, such as alkali metal amides (Li-N(i-propyl)$_2$ or lithium hexamethyldisilazane) to form the esters of formula I, and preparing therefrom by derivatization in a manner known per se the carboxylic acids, carboxylic acid halides and carboxylic acid salts. The desired enantiomers can be obtained from the racemates in a manner known per se by separating the racemates, for example by crystallization from addition salts of carboxylic acids using optically active bases. It is more advantageous to separate the racemates by treating esters of formula I with esterases.

A further object of the invention is a process for the preparation of compounds of formula I comprising the reaction of a compound of formula II,

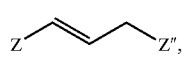

(II)

wherein Z and Z" are independently of one another chlorine, bromine or iodine, and preferably chlorine or bromine, in the presence of strong amine bases with a compound of formula III,

(III)

wherein X forms an ester group with the carbonyl substituent and $R_4$ is $C_1$–$C_6$alkyl, and if necessary derivatization of the resulting carboxylic acid esters of formula I to form carboxylic acids, carboxylic acid halides or carboxylic acid salts.

The strong amine bases are preferably alkali metal amides. It is expedient to carry out the reaction using ether as solvent and cooling to approximately ambient temperature. Cooling can mean down to about −20° C.

The compounds of formula Ia can also be obtained by asymmetric synthesis.

A further object of the invention is a process for the preparation of compounds of formula Ia comprising the reaction of a compound of formula IV,

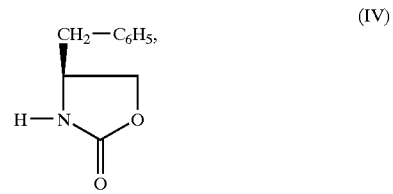

(IV)

with a carboxylic acid halide of formula $R_4CH_2$—CO—X, wherein $R_4$ is as defined above and X is chlorine, bromine or iodine, and reaction of the resulting compound of formula V,

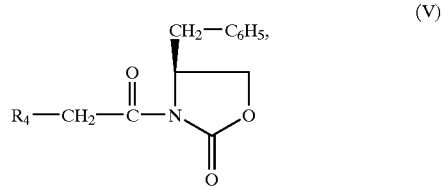

(V)

first with lithium hexamethyldisilazide and then with a compound of formula II,

(II)

wherein Z and Z" are independently of one another chlorine, bromine or iodine, followed by hydrolyzation of the resulting compound of formula VI

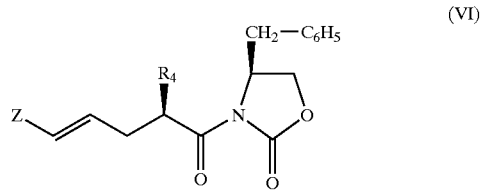

(VI)

with a base which isolates the salts or carboxylic acids of formula Ia, and if necessary derivatization of the carboxylic acids to form esters or halogenides.

5

An alkali metal base, for example LiOH, NaOH or KOH, is preferably used as the base, to accelerate the hydrolysis, an oxidizing agent may also be used, such as hydrogen peroxide. The individual process steps are analogous to processes that are known to a person skilled in the art and are described in more detail in the following examples.

A) Preparation of Compounds of Formula I

EXAMPLE A1

Preparation of

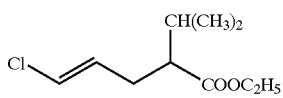
(A1)

An agitated solution of 77.7 ml diisopropylamine and 200 ml tetrahydrofuran is cooled to −20° C., and 200 ml 2.5 M N-hexyl lithium solution (in hexane) is added over a period of 15 minutes. The solution is stirred for 15 minutes at −20° C. and then, over a period 30 minutes, a solution of 75.3 ml ethyl isovalerate in 80 ml tetrahydrofuran is added dropwise. Agitation of the solution is continued for 10 minutes, and then 80 ml DMPU is added over a period of 10 minutes at −20° C. Addition of 8.2 g sodium iodide and 19.5 g trans-1,3-dichloropropene. The reaction mixture is agitated for a further 23 hours at −20° C., and then 500 ml 20% aqueous ammonium chloride solution is added. The mixture is extracted with tert-butyl methyl ether (2×400 ml) and the organic phases washed consecutively with 0.1 M sodium thiosulfate solution (1×500 ml), water (1×500 ml), and brine (1×500 ml). The combined organic phases are dried with 150 mg sodium sulfate and concentrated by evaporation. By means of distillation, title compound A1 is obtained as a colourless oil (86.1 g, 84%). $^1$H-NMR (400 MHz, CDCl$_3$, δ): 0.95 (m, 6H), 1.30 (t, 3H), 1.92 (m, 1H), 2.20–2.40 (m, 3H), 4.20 (m, 2H), 5.80–6.10 (m, 2H) ppm.

EXAMPLE A2

Preparation of

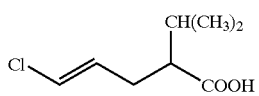
(A2)

A solution of 150.2 g A1, 500 ml ethanol and 500 ml 2N sodium hydroxide solution is agitated for 18 hours under reflux. The ethanol is evaporated from the reaction mixture, the aqueous solution acidified with 1N hydrochloric acid and extracted with diethyl ether (3×). The organic phases are dried with magnesium sulfate and concentrated by evaporation. By means of flash chromatography (SiO$_2$ 60F/dichloromethane/methanol 20:1), title compound A2 is obtained from the residue as a slightly orange oil (83.7 g, 65%): $^1$H-NMR (400 MHz, CDCl$_3$, δ): 1.03 (m, 6H) 1.98 (m, 1H), 2.20–2.45 (m, 3H), 5.80–6.10 (m, 2H) ppm.

6

B) Preparation of Compounds of Formula Ia

EXAMPLE B1

Preparation of

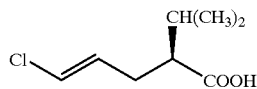
(B1)

5.0 g A2, 5.0 g cinchonidine and 1.98 ml triethylamine are transferred to 150 ml and agitated for 15 minutes under reflux. The oil bath is removed and the clear solution with a salt of B1 is inoculated with cinchonidine. Agitation is continued for 1 hour at ambient temperature and then for another 1 hour under ice cooling. The precipitate is filtered off, washed with twice 25 ml ice cold acetone and then dried in a vacuum at 50° C. until constant weight is attained. 6.16 g (46.3%) of the enriched salt of B1 is obtained with cinchonidine; melting point 149° C. After double recrystallization from acetone, 4.20 g (31.6%) of the enriched salt of B1 is obtained with cinchonidine, melting point 155° C. The salt obtained in this way is distributed between 250 ml diethyl ether and 50 ml 1N HCl. The aqueous phase is separated, the organic phase washed with saturated NaCl solution, dried with MgSO$_4$ and concentrated by evaporation in a vacuum. 1.58 g (31.6%) of enriched compound B1 is obtained as colourless oil.

EXAMPLE B2

Preparation of

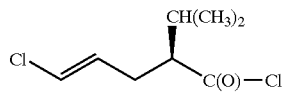
(B2)

4.42 ml oxalyl chloride is added to a solution of 4.54 g B1 in 25 ml toluene at ambient temperature. The reaction mixture is agitated for 15 minutes at ambient temperature, and then 0.052 ml N,N-dimethylformamide over a period of 1 minute. The reaction mixture is heated to reflux and agitated for 1 hour. The reaction solution is concentrated by evaporation and the residue distilled. Title compound B2 is obtained as a colourless oil. (4.43 g, 88%). $^1$H-NMR (400 MHz, CDCl$_3$, δ): 1.02 (d, 3H), 1.08 (d, 3H), 2.18 (m, 1H), 2.40 (m, 1H), 2.45 (m, 1H), 2.68 (m, 1H), 5.80–6.10 (m, 2H) ppm.

EXAMPLE B3

Preparation of

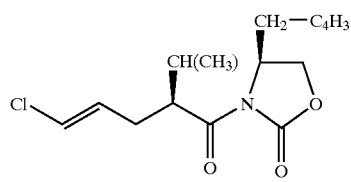
(B3)

A solution of 290 g 4S-benzyl-3-(3-methylbutyryl) oxazolidin-2-one in 0.58 l tetrahydrofuran is cooled to −78°

C., and 1.14 1 1 M lithium hexamethyldisilazide (in tetrahydrofuran) is added dropwise over a period of 65 minutes. The mixture is agitated for another hour at −78° C., and a prepared solution of trans-1-chloro-3-iodopropene in tetrahydrofuran is then added. The temperature is allowed to increase to 0° C. and agitation is continued for a further 20 hours. 500 ml 10% ammonium chloride solution is added to the reaction mixture, which is then extracted with diethyl ether (2×1 l). The organic phases are washed with water (1×1 l), dried with sodium sulfate and concentrated by evaporation. By means of flash chromatography ($SiO_2$ 60F/ethyl acetate/hexane 5:1), title compound B3 is obtained from the residue as a slightly orange oil (582 g, 78%): $^1$H-NMR (400 MHz, $CDCl_3$, δ): 0.85 (m, 6H), 2.02 (m, 1H), 2.3–255 (m, 2H), 2.75 (m, 1H), 3.30 (m, 1H), 3.88 (m, 1H), 4.18 (m, 2H), 4.70 (m, 1H), 5.80–6.10 (m, 2H), 7.15–7.40 (m, 5H) ppm.

Preparation of trans-1-chloro-3-iodopropene: 266.1 g sodium iodide is added to a solution of 184.7 g trans-1,3-dichloropropene in 0.58 l tetrahydrofuran and the mixture agitated for 30 minutes under exclusion of light at ambient temperature. The mixture is filtered until clear and the filtrate used directly.

EXAMPLE B4

Preparation of B1

To a solution of 155 g B3, 1.3 l tetrahydrofuran and 0.44 l water, agitated at 0° C., 315 ml 30% hydrogen peroxide solution is added dropwise over a period of 15 minutes. 22.1 g lithium hydroxide is added to the reaction mixture, then the cooling bath is removed and agitation is continued for 5 hours at 0–20° C. The reaction mixture is cooled again to 0° C., and a solution of 350 g sodium sulfite in 1.4 l water is added dropwise over a period of 30 minutes. The pH is adjusted to 9.8 by the addition of sodium hydrogencarbonate. The reaction mixture is filtered until clear and tetrahydrofuran evaporated from the filtrate. The aqueous solution obtained is washed with dichloromethane (3×3 l). The pH of the aqueous phase is adjusted to 3.0 with aqueous hydrochloric acid and then extracted with dichloromethane (3×2 l). The organic phases are dried with magnesium sulfate and concentrated by evaporation an the Rotavapor. By means of distillation, compound B1 is obtained from the residue as a colourless oil. (142 g, 87%). $^1$H-NMR (400 MHz, $CDCl_3$, δ): 1.02 (m, 6H), 1.98 (m, 1H), 2.25–2.45 (m, 3H), 5.85–6.10 (m, 2H) ppm.

EXAMPLE B5

Preparation of

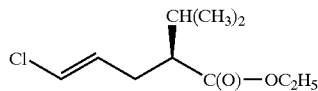

(B4)

A solution of 100 g A1 in 40 ml isopropanol is added to 1 l phosphate buffer (pH 7.0). In the presence of 2.0 ml (4400 U) pig liver esterase (Tech. Grade, Roche Diagnostics), the mixture is agitated at pH 8.0 and 40° C. until consumption of 262 ml 1.0 N NaOH. The reaction mixture is extracted with ethyl acetate (1×1 l and 2×0.5 l)). The organic phases are washed consecutively with 5% aqueous $Na_2CO_3$ solution (3×500 ml) and brine (1×0.5 l), dried with 300 g $Na_2SO_4$, concentrated by evaporation and dried in a vacuum. By means of distillation, title compound B4 is obtained from the residue as a colourless oil (45.4 g, 46%) with an ee value greater than 99%.

EXAMPLE B6

Preparation of (B1)

A solution of 150.2 g B4, 500 ml ethanol and 500 ml 2N sodium hydroxide solution is agitated for 18 hours under reflux. The ethanol is evaporated from the reaction mixture, the aqueous solution acidified with 1N hydrochloric acid and extracted with diethyl ether (3×). The organic phases are dried with magnesium sulfate and concentrated by evaporation. By means of flash chromatography ($SiO_2$ 60F/dichloromethane/methanol 20:1), title compound B1 is obtained from the residue as a slightly yellowish oil (0.88 g, 43%) with an ee value greater than 99%.

C) Examples of Application

EXAMPLE C1

Preparation of

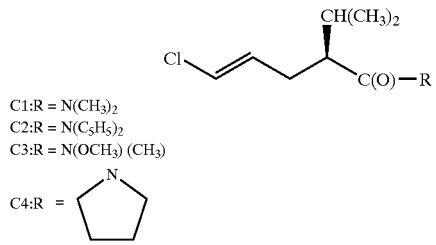

C1:R = $N(CH_3)_2$
C2:R = $N(C_5H_5)_2$
C3:R = $N(OCH_3)(CH_3)$
C4:R =

A solution of 1.53 g dimethylamine, 3.66 ml pyridine and 25 ml dichloromethane is cooled to 0° C., and then 4.42 g B2 in 25 ml dichloromethane is added dropwise at 0 to −10° C. The reaction mixture is agitated for a further 2 hours at 0° C. and then concentrated by evaporation on the Rotavapor. The residue is distributed between diethyl ether (2×) and 2N hydrochloric acid (3×), saturated sodium hydrogencarbonate solution (1×) and saturated saline solution. The organic fractions are combined, dried over sodium sulfate and concentrated. The residue is distilled, and title compound C1 is obtained as a colourless oil. (4.13 g, 89%). $[\alpha]^{25}_D$ —7.3 (c 1, chloroform). $^1$H-NMR (400 MHz, $CDCl_3$, δ): 0.90 (d, 3H), 0.95 (d, 3H), 1.92 (m, 1H), 2.20–2.30 (m, 1H), 2.35–2.50 (m, 2H), 2.98 (s, 3H), 3.04 (s, 3H), 5.80–6.10 (m, 2H) ppm.

Derivatives C2, C3 and C4 are prepared from the acid chloride B2 and the corresponding amines in the manner described in example C1.

EXAMPLE C2

Preparation of

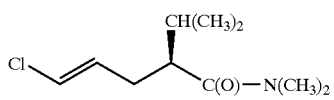

(C1)

A solution of 0.435 g dimethylamine and 6 ml toluene is slowly added to a mixture of 5 ml trimethyl aluminium (2M in toluene) and 5 ml toluene at −15° C. The temperature is allowed to rise to ambient temperature for 1 hour, and a solution of 1.79 g B4 in 5 ml toluene is added. Agitation of the reaction mixture is continued for a further 22 hours at 80° C. The reaction mixture is cooled to ambient temperature, and 20 ml 0.5 N hydrochloric acid is slowly added (exothermic reaction). The mixture is extracted 3 times with 30 ml toluene, and the organic phases are washed consecutively with 2×30 ml water and 30 ml saturated aqueous sodium hydrogen sulfate solution. The combined organic phases are dried with magnesium sulfate and concentrated by evaporation on the Rotavapor. By means of flash chromatography ($SiO_2$ 60F/ethyl acetate/hexane 1:2), title compound C1 is obtained from the residue as a colourless oil (1.50 g, 84%).

What is claimed is:

1. A compound of formula Ia,

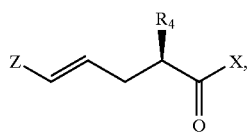

(Ia)

wherein $R_4$ is $C_1$–$C_6$alkyl, Z is chlorine, bromine or iodine, and X is —OH, chloride, bromide or iodide, or X forms an ester group with the carbonyl substituent, or a carboxylate salt thereof.

2. A compound according to claim 1, wherein $R_4$ is $C_1$–$C_4$alkyl.

3. A compound according to claim 1, wherein $R_4$ is methyl, ethyl, n- or i-propyl, or n-, i- or t-butyl.

4. A compound according to claim 1, wherein $R_4$ is i-propyl.

5. A compound according to claim 1, wherein Z is Cl.

6. A compound according to claim 1, wherein X is a substituent of formula $R_7O$—, wherein $R_7$ is an organic group with 1 to 18 C-atoms, optionally containing O or N or both O and N atoms.

7. A compound according to claim 6, wherein $R_7$ is $C_1$–$C_4$alkyl.

8. A compound according to claim 1, wherein X is chloride or bromide.

9. A compound according to claim 1, wherein the salts of the carboxylic acids are alkali metal or alkaline earth metal salts or ammonium salts.

10. A compound according to claim 1, wherein Z is chlorine, $R_4$ is $C_1$–$C_4$alkyl, and X is OH, Cl, Br or $C_1$–$C_4$alkoxy.

11. A compound according to claim 10, wherein $R_4$ is i-propyl.

12. A compound according to claim 1, wherein Z is chlorine, $R_4$ is i-propyl, and X is OH, Cl, Br, methoxy or ethoxy.

13. A compound according to claim 12, wherein Z is chlorine, $R_4$ is i-propyl, and X is Cl or Br.

14. A process for the preparation of a compound of formula Ia, which comprises reacting a compound of formula IV,

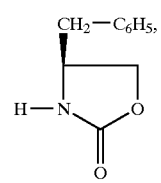

(IV)

with a carboxylic acid halide of formula $R_4CH_2$—CO—X, wherein $R_4$ is $C_{1-6}$ alkyl and X is chlorine, a compound of formula V,

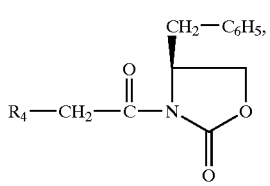

(V)

reacting the compound of formula V with lithium hexamethyldisilazide followed by reacting the resulting compound with a compound of formula II,

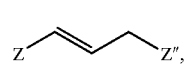

(II)

wherein Z and Z″ independently of one another chlorine, bromine or iodine, to produce a compound of formula VI,

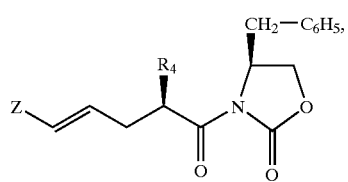

(VI)

and hydrolyzing the compound of formula VI with a base which isolates the salts or carboxylic acids of formula Ia, and optionally derivatizing the carboxylic acids to form esters or halides.

* * * * *